United States Patent
Elliott et al.

(10) Patent No.: US 7,867,505 B2
(45) Date of Patent: *Jan. 11, 2011

(54) FOUNDATION

(75) Inventors: Russell Phillip Elliott, Egham (GB); Raj Kumar Gabbi, Farnham (GB); Neil John Jones, Staines (GB); Jennifer Clare Cantor, Addlestone (GB)

(73) Assignee: The Procter & Gamble Company, Cincinnati, OH (US)

( * ) Notice: Subject to any disclaimer, the term of this patent is extended or adjusted under 35 U.S.C. 154(b) by 558 days.

This patent is subject to a terminal disclaimer.

(21) Appl. No.: 11/134,959

(22) Filed: May 23, 2005

(65) Prior Publication Data

US 2006/0263310 A1   Nov. 23, 2006

(30) Foreign Application Priority Data

May 24, 2004   (EP) .................. 04253035

(51) Int. Cl.
*A61K 8/02* (2006.01)

(52) U.S. Cl. .................. 424/401; 424/63

(58) Field of Classification Search .................. None
See application file for complete search history.

(56) References Cited

U.S. PATENT DOCUMENTS

| | | | | |
|---|---|---|---|---|
| 5,266,321 A | * | 11/1993 | Shukuzaki et al. | 424/401 |
| 5,368,639 A | * | 11/1994 | Hasegawa et al. | 106/490 |
| 5,458,681 A | * | 10/1995 | Hasegawa et al. | 106/490 |
| 5,945,092 A | * | 8/1999 | Krog et al. | 424/64 |
| 6,174,983 B1 | * | 1/2001 | Czech et al. | 528/25 |
| 6,258,345 B1 | * | 7/2001 | Rouquet et al. | 424/64 |
| 6,342,239 B1 | | 1/2002 | Shimizu et al. | |
| 6,482,441 B1 | * | 11/2002 | Hasegawa et al. | 424/490 |
| 6,524,598 B2 | * | 2/2003 | Sunkel et al. | 424/401 |
| 6,548,074 B1 | * | 4/2003 | Mohammadi | 424/401 |
| 7,563,452 B2 | | 7/2009 | Kuroda | |
| 7,722,899 B2 | | 5/2010 | Ono | |
| 2002/0018790 A1 | | 2/2002 | Motley et al. | |
| 2002/0028184 A1 | | 3/2002 | Sunkel et al. | |
| 2002/0028223 A1 | | 3/2002 | Motley et al. | |
| 2003/0108498 A1 | | 6/2003 | Stephens et al. | |
| 2004/0091440 A1 | | 5/2004 | Kamei et al. | |
| 2005/0260147 A1 | | 11/2005 | Elliott et al. | |
| 2005/0260148 A1 | | 11/2005 | Elliott et al. | |
| 2005/0260149 A1 | | 11/2005 | Elliott et al. | |
| 2005/0281770 A1 | | 12/2005 | Elliott et al. | |

FOREIGN PATENT DOCUMENTS

| | | |
|---|---|---|
| EP | 0197870 A | 10/1986 |
| EP | 1213006 A | 6/2002 |
| EP | 1314415 A | 5/2003 |
| EP | 1405624 A | 4/2004 |
| EP | 1416016 A | 5/2004 |
| JP | 10120524 | 5/1998 |
| JP | 2001058935 | 3/2001 |
| JP | 2002080748 | 3/2002 |
| JP | 2002/363445 | 12/2002 |
| JP | 3736848 | 1/2006 |
| WO | WO 02/100356 | 12/2002 |
| WO | WO 03/053396 A1 | 7/2003 |
| WO | WO 03/075864 | 9/2003 |

OTHER PUBLICATIONS

Database Caplus 'Online! Chemical Abstracts Service, Columbus, Ohio, US; Sato, Yumiko et al:Transparent or translucent emulsified cosmetic stock; XP002302813.

Database Caplus 'Online! Chemical Abstracts Service, Columbus, Ohio, US; Itani, Mamoru et al: "Manufacture of Cosmetic Compositions containing stably dispersed inorganic particles, and their use for sunscreens"; XP002302812.

Anonymous: "Neue Sonnenschutzformulierungen" Research Disclosure, Kenneth Mason Publications, Hampshire, GB, vol. 466, No. 29, Feb. 2003, XP007132193 ISSN: 0374-4353.

* cited by examiner

*Primary Examiner*—Sreeni Padmanabhan
*Assistant Examiner*—Layla Soroush
(74) *Attorney, Agent, or Firm*—Megan C. Hymore; S. Robert Chuey; Carl Roof

(57) ABSTRACT

A cosmetic composition is provided comprising
(a) metal oxide particles; and
(b) greater than 1.7% by weight of the cosmetic composition of cross-linked organopolysiloxane elastomer,
wherein organo-functionalised silicone fibrils are bonded to and extend away from the surface of the metal oxide particles.

36 Claims, No Drawings

FOUNDATION

FIELD OF THE INVENTION

The present application concerns cosmetic compositions, especially cosmetic foundation compositions.

BACKGROUND OF THE INVENTION

It is known to include fatty or oleophilic materials, including silicones, in cosmetic products to provide occlusive (moisture-retention) properties, improved feel properties, as solvents and for other reasons. It is also known to include metal oxide particle benefit agents in cosmetic compositions—depending on the type of oxide, the particle size and/or configuration, agents may, for example, provide pigmentary and/or sunscreening benefits. In order to marry the benefits of both types of component, it is a natural step to consider including both types of component in a single composition. This presents difficulties, however, because metal oxide particles generally do not readily disperse in a hydrophobic matrix. To overcome this difficulty, it is known to stabilise metal oxide particles within an oleophilic phase by adding emulsifying agents to a composition.

Emulsifiers in low dielectric constant media may use steric effects to provide stabilisation and prevent flocculation. To be more precise, the emulsifier coats the free surface of the particle with hydrophilic tails and extends oleophilic chain into the medium and the chain acts to prevent agglomeration by osmotic effects: as two particles approach one another, the chains overlap and cause a temporary increase in polymer concentration. This increase causes an osmotic stress that forces fluid between the particles, thereby causing them to separate.

The addition of free emulsifier to a composition may, however, not be sufficient to ensure a good particle dispersion throughout the life cycle of the product. If the concentration of emulsifier is too low then the osmotic stress will be correspondingly low and, as two particles approach one another, the emulsifier may bridge the particles actually promoting agglomeration. If, on the other hand, the concentration of emulsifier is too high, then the osmotic stress behaviour may be reversed leading to depletion flocculation. In this scenario, the concentration of free emulsifier may be so high that, as particles approach one another, free emulsifier may be forced out from between them. The concentration difference may create an osmotic stress that draws fluid out of the space between the particles thereby promoting agglomeration.

An ideal level of emulsifier exists for any system but small changes in that system may cause the the amount of emulsifier to move away from the optimum, thereby leading to the above-described problems. Especially in the case of a product that is required to dry down in use, it is almost impossible to achieve an ideal level of emulsifier at all time points, because, during the drying process, the emulsifier concentration continually increases. In other words, the use of non-bonded coating on the surface of the particle means that for any system the emulsifier concentration must be sub-optimal at some stage in its life cycle.

To overcome the disadvantages of non-bonded emulsifier coatings, use of a coating which is bonded to the surface of a particle may be employed. Bonding may prevent the emulsifier bridging and, since the there is no free emulsifier in the solution, depletion flocculation may be avoided. In addition, since it is no longer necessary to prevent diffusion of emulsifier away from the surface, there is no requirement to control the hydrophilic/lipophilic balance (HLB) of the emulsifier. As a result, the molecules in a bonded coating may have longer tails than non-bonded emulsifiers, which, in turn, may increase the steric stabilisation effect.

It is known to formulate compositions comprising metal oxide particles which have been coated with bonded emulsifier to provide steric stabilisation. Such formulations are disclosed in the article entitled "Development of Novel Silicones for Powder Surface Treatment" by Masaneo Kamei in the Fragrance Journal, p. 81-85, 2002-6. The cosmetic compositions disclosed in that article are difficult to apply to skin, however, which may result in the benefit achieved by the metal oxide particle benefit agent being less even than it should be.

SUMMARY OF THE INVENTION

According to a first aspect of the invention, a cosmetic composition is provided comprising:
(a) metal oxide particles; and
(b) greater than 1.7% by weight of the cosmetic composition of cross-linked organopolysiloxane elastomer, wherein organo-functionalised silicone fibrils are bonded to and extend away from the surface of the metal oxide particles.

As used herein, the term "bond" includes, but is not limited to, chemical bonds, such as chemisorption and covalent bonds. The term "bonded" is to be interpreted accordingly.

According to a second aspect of the invention, cosmetic foundation compositions are provided comprising cosmetic compositions according to the first aspect of the invention.

DETAILED DESCRIPTION OF THE INVENTION

All weights, measurements and concentrations herein are measured at 25° C. on the composition in its entirety, unless otherwise specified.

As used herein in relation to metal oxide sunscreen particles, all weights of doping or coating materials are given as percentages of the weight of the underlying metal oxide particle which is thus doped or coated. This definition applies even when the doping or coating material is, itself, a metal oxide. Thus, if the particles weigh x grammes and the coating or doping material weighs y grammes, the percentage weight of the coating or doping material is y/x*100.

As used herein in relation to the cosmetic composition, the percentage weight of the metal oxide sunscreen particles is the combined weight of the underlying metal oxide particle and any doping or coating divided by the weight of the entire cosmetic composition. Thus, if the particles weigh x grammes, the coating or doping material weighs y grammes and the entire cosmetic composition (including the coated or doped metal oxide particles) weighs z grammes, then the percentage weight of the metal oxide particle is (x+y)/z*100.

Unless otherwise indicated, all percentages of compositions referred to herein are weight percentages of the total composition (i.e. the sum of all components present) and all ratios are weight ratios.

Unless otherwise indicated, all polymer molecular weights are number average molecular weights.

Reference herein to the percentage weight of cross-linked organopolysiloxane elastomer in a composition is a reference to the percentage weight of solid organopolysiloxane elastomer in that composition, not to the percentage weight of solid organopolysiloxane elastomer plus solvent in the composition. This is stated for the avoidance of doubt, since commercially available organopolysiloxane elastomers are often sold in combination with a solvent.

Unless otherwise indicated, the content of all literature sources referred to within this text are incorporated herein in full by reference.

Except where specific examples of actual measured values are presented, numerical values referred to herein should be considered to be qualified by the word "about".

Metal oxide primary particles in the nano- and micrometer size range have high surface areas per unit volume and are correspondingly reactive leading to their agglomeration to form secondary particles. This agglomeration is inevitable and, up to a point, may not be undesirable—minute, nanometer-size particles do not scatter light, making them less suitable as UV-A sunscreens. If the secondary particle size is unchecked, however, then the particles generated may not have the required properties and the composition may not provide an even benefit in use. In addition, particularly in the case of sunscreens, excessive agglomeration may alter or significantly reduce the benefit obtained: it is believed that the primary particle size drives the overall surface area of the secondary particles, with smaller primary particles generally giving rise to secondary particles of greater surface area. Secondary particle surface area, in turn, is believed to drive absorption of UV-B radiation—the larger the secondary particle surface area, the greater the degree of UV-B absorption. Secondary particle size, on the other hand, is considered to drive scattering of UV-A radiation, with larger particles reflecting more. Without wishing to be bound by theory, it is believed that agglomeration of secondary particles may reduce both UV-B absorption and UV-A scattering, thereby significantly affecting the sunscreening benefit: agglomeration of secondary particles drives down overall secondary particle surface area, thereby reducing the degree of UV-B absorption; in addition, whilst UV-A reflection does increase with secondary particle size, the overall number of secondary particles drops with increasing agglomeration, thereby reducing UV-A reflection too.

In order to reduce or prevent agglomeration of secondary particles, the metal oxide particles are provided with a coating of organo-functionalised silicone fibrils, which fibrils are bonded to and extend away from the surface of the metal oxide particles into the carrier medium. As already discussed, it is believed that, as coated metal oxide particles approach one another, their fibrils may become enmeshed. The resulting high concentration of organo-functionalised siloxane polymer in the region where that enmeshing is occurring generates a high osmotic pressure causing carrier fluid to flow in between the adjacent particles and force them apart.

The fibrils may advantageously be attached by treating the metal oxide particles with an organo-functionalised silicone polymer comprising a reactive moiety selected from the group consisting of amino, imino, halogen, hydroxyl, and alkoxyl such that the organo-functionalised silicone polymer becomes adsorbed to the surface of the metal oxide polymer.

Advantageously, the organo-functionalised silicone polymer comprises from 5 to 100, preferably from 25 to 50 silicone repeating units. Polymers of this size project into and may flow freely in the carrier medium, thereby avoiding agglomeration further. As used herein, a "silicone repeating unit" or "silicone unit" means

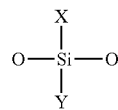

where each of X and Y is, independently, an alkyl group or any functional group.

Preferably, the organo-functionalised silicone polymer has a ratio (Mw/Mn) of weight-average molecular weight (Mw) to number-average molecular weight (Mn) from 1.0 to 1.3. Without wishing to be bound by theory, it is believed to be important that the surface coating be as even as possible to maximise the osmotic pressure and also to avoid bridging flocculation by comparatively longer polymer chains.

The organo-functionalised silicone polymer may be a linear organofunctionalised silicone polymer. In this case, it is preferred to locate the reactive moiety at one end of its molecular chain.

Alternatively, the organo-functionalised silicone polymer may be a branched chain organofunctionalised silicone polymer. In this case, the reactive moiety is preferably located on a side chain. Advantageously, the side chain on which the reactive moiety is found is located within five silicone repeating units, preferably within three silicone repeating units of one end of the silicone backbone.

To manufacture the coated metal oxide particles, organo-functionalised silicone polymer, as specified above, an organic solvent which dissolves said organo-functionalised silicone polymer, and metal oxide are mixed, then dried by heating. The organo-functionalised silicone polymer should be used in an amount from 0.1 wt % to 30 wt %, preferably from 1 wt % to 15 wt %, more preferably from 2 wt % to 8 wt % of the metal oxide particles to be treated, depending on its particle diameter and specific surface area.

An appropriate organic solvent should be selected in consideration of its flash point and ignition point, and the surface activity and heat stability of the metal oxide particles for surface treatment. Preferred examples of the organic solvent include ethers, ketones, halogenated hydrocarbons, aliphatic hydrocarbons, and alcohols and mixture thereof with other solvents such as water. The organic solvent should be used in an amount of 1-50 wt % to the metal oxide particles.

The mixing of the organo-functionalised silicone polymer, organic solvent, and metal oxide particles may be accomplished by putting them together into an ordinary mixer, or by spraying the organo-functionalised silicone polymer onto a mixture of the organic solvent and metal oxide particles. The heating of the mixture should be carried out in an adequate manner in consideration of the heat resistance of the metal oxide particles and the kind of organic solvent used.

Examples of suitable organo-functionalised silicone polymers include dimethylpolysiloxysilazane, α-monohydroxysiloxane, α,ω-dihydroxypolydimethylsiloxane, α-monoalkoxypolydimethylsiloxane, α,ω-dihdroxypolydimethylsiloxane, α-dialkoxypolydimethylsiloxane, α-trialkoxypolydimethylsiloxane, α,ω-hexa-alkoxypolydimethylsiloxane, dimethylpolysiloxy chloride, dimethylpolysiloxy bromide, and dimethylpolysiloxy iodide. Preferred among those examples are .alpha.-monoalkoxypolydimethylsiloxane, .alpha.-dialkoxypolydimethylsiloxane, alpha.-trialkoxypolydimethylsiloxane, α-monohydroxymethylphenyl siloxane, α-trialkoxypolymethyl hexyl siloxane and methyl styryil/dimethyl polysiloxy bromide. They are adsorbed to the pigment very easily, and upon adsorption they impart a smooth feel to the treated pigment. The reactive group in the organo-functionalised silicone may be joined to the silicon atom directly or indirectly thorough a substituent group.

Commercially available organo-functionalised silicone polymers which may be employed to coat the metal oxide particles include the following materials: X-24-9826, X-24-9171 and X-24-9174 manufactured by the Shin Etsu Co. Ltd; TSL 8185 and TSL 8186 manufactured by Toshiba Silicone Co. Ltd.; SIO6645.0 manufactured by Chisso Corporation; KBM-3103 manufactured by Shin-Etsu Chemical Co. Ltd.; A-137 manufactured by Nippon Unicar Co. Ltd.

In addition to providing the metal oxide particles with fibrils, they may also be provided with a hydrophobic coating to improve the particles' dispersion in hydrophobic carrier medium. The hydrophobic coating may be applied as a pre-treatment, prior to provision of the fibrils, or as a post-treatment, after provision of the fibrils. Advantageously, the metal oxide particles comprise from 2 to 25%, preferably from 5% to 15%, more preferably from 7% to 12% hydrophobic coating by weight of the metal oxide particles.

Advantageously, the hydrophobic coating may be made by applying a mixture of one or more of the following materials and isopropyl alcohol onto the metal oxide powder and drying at 150° C. for 3 hours: reactive organo-polysiloxane, polyolefin (including polyethylene and polypropylene), hydrogenated lecithin and salts thereof, N-acylamino acid and salts thereof and dextrin fatty acid esters. Preferably, the reactive organo-polysiloxane comprises organo hydrogen polysiloxane, triorgano siloxy silicic acid and organopolysiloxane modified at both terminal ends with trialkoxy groups. Commercially available materials falling into the category of reactive organo-polysiloxanes include KF-99, KF-9901, KF-7312F, KF-7312-J, KF-7312K, KF-9001, KF-9002, X-21-5249 and X-21-5250 manufactured by the Shin-Etsu Chemical Company Ltd; SH-1107, DC593, BY-11-015, BY-11-018 and BY-11-022 manufactured by Dow Corning Toray Silicone Co. Ltd.; TSF484, TSF483 and TSF4600 manufactured by Toshiba Silicone Co. Ltd.; FZ3704 and AZ6200 manufactured by Nippon Unicar Co. Ltd.

The hydrophobic coating is not limited to those described in the preceding paragraph and alternative hydrophobic coatings known to the skilled person may be employed instead. Such coatings may include trialkoyl isopropyl titanate, preferably triisostearoyl isopropyl titanate and perfluoro coatings, preferably polyperfluoroethoxymethoxy PEG-2 phosphate.

Some coatings may both provide hydrophobic properties and exhibit fibrils to provide steric stabilisation to avoid flocculation. Commercially available coatings falling into this category include KF9908 (Triethoxysilylethyl Polydimethylsiloxyethyl Dimethicone), KF9909 (Triethoxysilylethyl Polydimethylsiloxyethyl Hexyl Dimethicone) and KP575 (Acrylate/Tridecyl Acrylate/Triethoxysilylproplyl Methacrylate/Dimethicone Methacrylate Copolymer) from the Shin Etsu Co Ltd.

Cosmetic compositions according to the invention comprise metal oxide particles, which may comprise particles of any suitable metal oxide. Preferably, the metal oxide particles are selected from the group consisting of titanium oxide, zinc oxide, zirconium oxide, yellow iron oxide, black iron oxide, red iron oxide, chromium oxide, chromium hydroxide, zirconium oxide and cerium oxide. More preferably, the metal oxide particles may be selected from titanium dioxide particles, zinc oxide particles and mixtures thereof. More preferably still, the metal oxide particles comprise titanium dioxide particles.

As discussed above, the primary particle size is important in determining the surface area of the secondary particles. Advantageously, the metal oxide particles according to the invention have a number weighted average primary particle size from 10 to 500 nm, preferably from 15 to 100 nm, more preferably from 20-65 nm, yet more preferably from 25 to 40 nm. Within the defined ranges, secondary particles having high surface areas and beneficial UV-B absorption properties may be formed.

As used herein, the term "primary particle size" means metal oxide crystal size, as determined by x-ray diffraction. It is based on measuring the broadening of the strongest rutile line.

Furthermore, the metal oxide particles may have a number weighted average secondary particle size from 0.005 to 100 μm, preferably from 0.015 to 10 μm, more preferably from 0.05 to 1 μm. Sunscreening metal oxides may advantageously have a number weighted average secondary particle size from 100 to 250 nm. Pigmentary metal oxides may advantageously have a number weighted average secondary particle size from above 250 nm to 500 nm.

The number weighted average secondary particle size is determined using a Nicomp 370 Sub Micron Particle Sizer.

Cosmetic compositions according to the invention may comprise from 0.1 wt % to 45 wt % metal oxide particles. If metal oxide pigments are present, then the cosmetic composition preferably comprises from 0.05 wt % to 30 wt %, preferably from 1 wt % to 20 wt % metal oxide pigments. If metal oxide sunscreen actives are present, then the cosmetic composition preferably comprises from 0.05 wt % to 15 wt %, preferably from 0.5 wt % to 10 wt %, more preferably from 1 wt % to 5 wt % metal oxide sunscreen actives.

Minute metal oxide particles have a highly reactive surface that can cause unwarranted chemical or photochemical reactions. To counter this effect, it is known to dope these surfaces with one or more other materials such as silica, or metal oxides, such as alumina, to reduce the reactivity of the surface. This surface treatment may typically represent from 15 to 30% by weight of the metal oxide particle. Advantageously metal oxide particles comprised within cosmetic compositions according to the invention may be so-doped.

Commercially available sunscreens which may be employed in cosmetic compositions according to the invention include KQ-1 from Ishihara Corp., M262 from Kemira Corp. and TTO S-3 and TTO S-4 from Ishihara Corp. Iron oxide pigments suitable for use herein include methicone treated iron oxides available from Warner Jenkinson.

In a highly preferred embodiment, the following materials are employed: SAS/TTO S-3/D5 from Miyoshi Kasei which has an average primary particle of about 15 nm and SAI/NAI TR10 with a primary particle size of about 100 nm. These commercially available materials are pre-coated with fibrils according to the invention.

Cross-linked organopolysiloxane elastomer may be present in an amount which is greater than 1.7% up to 15%, preferably from 2% to 10%, more preferably from 2.2 to 5% by weight of the cosmetic composition. As stated above, these are the amounts of solid organopolysiloxane elastomer in the composition. Surprisingly, the present inventors have established that above 1.7% elastomer, and especially in the preferred ranges, the evenness of the benefit provided by the metal oxide particles improves.

The compositions of the present invention may comprise emulsifying cross-linked organopolysiloxane elastomer, non-emulsifying cross-linked organopolysiloxane elastomer or mixtures thereof. If present, then the emulsifying cross-linked organopolysiloxane elastomer is present in an amount from 0.01 to 15%, preferably from 0.01 to 1% by weight of the composition. In addition and if present, the non-emulsifying cross-linked organopolysiloxane elastomer is advantageously present in an amount from 0.01 to 15%, preferably from 2-5% by weight of the cosmetic composition.

As used herein, the term "non-emulsifying", when employed in relation to cross-linked organopolysiloxane elastomer includes cross-linked organopolysiloxane elastomer which comprise no polyoxyalkylene or polyglyceryl units.

As used herein, the term "emulsifying" when employed in relation to cross-linked organopolysiloxane elastomer includes cross-linked organopolysiloxane elastomer which comprise at least one polyoxyalkylene (e.g., polyoxyethylene or polyoxypropylene) or polygyceryl unit.

No specific restriction exists as to the type of curable organopolysiloxane composition that can serve as starting material for the cross-linked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane; condensation-curing organopolysiloxane compositions which cure in the presence of an organotin compound or a titanate ester, by a condensation reaction between an hydroxyl-terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Preferred non-emulsifying organopolysiloxane compositions are dimethicone/vinyl dimethicone crosspolymers. Such dimethicone/vinyl dimethicone crosspolymers are supplied by a variety of suppliers including Dow Corning (DC 9040, DC 9041), General Electric (SFE 839 and Velvesil materials), Shin Etsu (KSG-15, 16, 18 [dimethicone/phenyl vinyl dimethicone crosspolymer]), Grant Industries (Gransil (™) line of materials), lauryl dimethicone/vinyl dimethicone crosspolymers supplied by Shin Etsu (e.g., KSG-31, KSG-32, KSG-41, KSG-42, KSG-43, and KSG-44).

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes cross-linked by Si—H sites on a molecularly spherical MQ resin. Examples of commercially available emulsifying cross-linked organopolysiloxane elastomers include KSG-21 (comprising 27% solid organopolysiloxane elastomer) and KSG-210 (comprising 24% solid organopolysiloxane elastomer) and KSG-320 from the Shin-Etsu Chemical Company Ltd. Commercially available examples of emulsifying cross-linked organopolysiloxane elastomers comprising polyglyceryl units are KSG 710 and KSG-800 from the Shin-Etsu Chemical Company Ltd.

Advantageously, cosmetic compositions according to the invention comprise an oil. Oil may be present in an amount from 7% to 80% by weight of the cosmetic composition.

The oil may be selected from the group consisting of volatile oils, non-volatile oils and mixtures thereof.

As used herein, the term "non-volatile" when employed in relation to an oil includes oils that fulfil at least one of the following definitions: (a) the oil exhibits a vapour pressure of no more than about 0.2 mm Hg at 25° C. and one atmosphere pressure; (b) the oil has a boiling point at one atmosphere of at least about 300° C.

As used herein, the term "volatile" when employed in relation to oils includes materials that are not "non-volatile" as previously defined herein.

Any non-volatile oil adhering to the above definition may be included in cosmetic compositions according to the invention. Such non-volatile oils may include silicone oils, both functionalised and non-functionalised, hydrocarbon oils and mixtures thereof. Non-volatile oil may be present in an amount from 0 to 20%, preferably from 1 to 10% by weight of the cosmetic composition.

Volatile oils which may be included in cosmetic compositions according to the invention may include silicone oils, both functionalised and non-functionalised, hydrocarbon oils and mixtures thereof. Volatile oil useful in the present invention may exhibit one or more of the following characteristics—it may be saturated or unsaturated, have a straight or branched chain or a cyclic structure.

Examples of volatile hydrocarbons which may be incorporated into cosmetic compositions according to the invention include polydecanes such as isododecane and isodecane (e.g., Permethyl-99A which is available from Presperse Inc.) and the $C_7$-$C_{15}$ isoparaffins (such as the Isopar Series available from Exxon Chemicals).

Examples of volatile silicone oils which may be incorporated into cosmetic compositions according to the invention include cyclic volatile silicones corresponding to the formula:

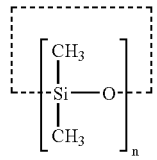

wherein n is from about 3 to about 7 and linear volatile silicones corresponding to the formula:

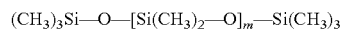

wherein m is from about 1 to about 20 preferably from 3 to 12.

Preferably, the cyclic volatile silicone is cyclopentasiloxane or cyclohexasiloxane.

Linear volatile silicones generally have a viscosity of less than about 5 centistokes at 25° C.; cyclic silicones generally have viscosities of less than about 10 centistokes at 25° C.

Examples of commercially available volatile silicone oils include the following cyclomethicones: Dow Corning 200, Dow Corning 244, Dow Corning 245, Dow Corning 344, and Dow Corning 345 (commercially available from Dow Corning Corp.); SF-1204 and SF-1202 Silicone Fluids (commercially available from G. E. Silicones), GE 7207 and 7158 (commercially available from General Electric Co.); and SWS-03314 (commercially available from SWS Silicones Corp.). Other examples of commercially available methyl silsesquioxanes available as TMF 1.5 fluid from Shin-Etsu Chemical Co; SILCARE SILICONES, for example phenyl substituted silsesquioxanes available as Silcare 15M60, n-Octyl substituted silsesquioxanes available as Silcare 31M60 and 31M50, hexyl methicone, caprylyl methicone and lauryl methicone available as Silcare 41M10, 41M15 and 41M20 respectively from Clariant.

Volatile oil may be present in an amount from 7 to 70%, preferably from 10% to 50%, more preferably 20% to 40% by weight of the cosmetic composition.

In one advantageous embodiment, it is preferred that the volatile oil comprise a mixture of volatile cyclic silicone and volatile linear dimethicone of viscosity from 2 to $50 \times 10^{-6}$ m$^2$/s (2-50 cst), more preferably from 3 to $50 \times 10^{-6}$ m$^2$/s (3-5 cst), more preferably still from 3 to $50 \times 10^{-6}$ m$^2$/s (4 cst). Without wishing to be bound by theory it is believed that, during dry-down the linear dimethicone may remain on the skin longer to keep the metal oxide particles wetted, thereby reducing agglomeration. Agglomeration is responsible for colour drift, in the case of pigments, and reduced SPF efficacy, in the case of sunscreens.

Advantageously, the ratio of volatile cyclic silicone to volatile linear dimethicone is from 1:1 to 25:1, preferably from 5:1 to 10:1.

Preferred examples of linear dimethicones useful include DC200 5 cst, DC1630 and DC5-2117, more preferably, the linear dimethicone comprises DC5-2117.

Cosmetic compositions according to the invention may be formulated as anhydrous products or as emulsions. If the cosmetic compositions are formulated as emulsions, those emulsions may be water-in-oil (water-in-silicone) emulsions or oil-in-water (silicone-in-water) emulsions, but are preferably water-in silicone emulsions.

Advantageously, the cosmetic compositions according to the invention are formulated as water-in-silicone emulsions that contain from 0.1 to 70%, preferably from 1 to 50%, more preferably from 5 to 40% water.

Cosmetic compositions according to the invention, whether or not they are in the form of an emulsion, may comprise emulsifier. The emulsifier may be selected from the group consisting of nonionic, anionic, cationic, zwitterionic and amphoteric emulsifiers and mixtures thereof. Suitable emulsifiers are disclosed in McCutcheon's Detergents and Emulsifiers, North American Edition, pages 317-324.

In the event that the cosmetic composition according to the invention is a water-in-silicone emulsion, then preferred emulsifiers are selected from the group consisting of polyoxyalkylene copolymers (also known as silicone polyethers), polyglyceryl copolymers and mixtures thereof. Polyoxyalkylene copolymers are described in detail in U.S. Pat. No. 4,268,499. More preferred polyethers include PEG/PPG-18/18 Dimethicone available as blend with cyclopentasiloxane as DC5225C or DC5185; PEG 9 Dimethicone, available as KF6017 or KF6028 from Shin-Etsu. A preferred polyglyceryl emulsifier is available as KF6100 and KF6104 from Shin-Etsu Inc.

In one embodiment, it is preferred that cosmetic compositions according to the invention comprise only polyglyceryl copolymer emulsifiers and no polyoxyalkylene emulsifiers. This is because polyoxyalkylene emulsifiers may break down to release ethylene glycol and aldehydes which may give rise to increased sensitivity on the skin of some consumers.

The total concentration of the emulsifier may be from 0.01% to about 15%, more preferably from about 0.1% to about 10% of the formulation, even more preferably from 1.0% to about 5% and more preferably still from about 1.0% to about 3%, by weight of the composition.

Cosmetic compositions according to the present invention may optionally contain spherical particles having an average particle diameter from 1 to 50 μm, preferably from 5 to 20 μm. As used herein in relation to the spherical particles, the particle diameter shall be understood to be that of primary particles.

Preferred spherical particles include, but are not limited, to polymeric particles chosen from the methylsilsesquioxane resin microspheres such as for example those sold by GE silicone under the name Tospearl 145A or Tospearl 2000; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat Cos, polystyerene microspheres such as for example those sold by Dyno Particles under the name Dynospheres, ethylene acrylate copolymer sold by Kobo under the name Flo-Bead EA209 and mixtures thereof. Also found to be useful is Ronasphere LDP from Kobo Inc. Polyurethane particles BPD500 sold by Kobo Inc. may also be employed.

If present, the spherical particles may be included in the cosmetic compositions according to the invention at a concentration of from about 0.01% to about 40%, more preferably from about 1% to about 10%, more preferably still from about 1% to about 5%.

Cosmetic compositions according to the present invention may further comprise a skin-conditioning agent. These agents may be selected from humectants, exfoliants or emollients and may be present from about 0.01% to 30%, preferably from about 1% to about 20%, more preferably from about 1% to 10% by weight of the cosmetic composition.

Humectants which may be included in cosmetic compositions according to the invention include polyhydric alcohols such as glycerine, propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerine and mixtures thereof. Most preferably the humectant comprises glycerine.

In addition, hydrophilic gelling agents such as those selected from the group consisting of the acrylic acid/ethyl acrylate copolymers, carboxyvinyl polymers (such as those sold by the B.F. Goodrich Company under the Carbopol trademark, polyacrylamides (such as those available from Seppic as Seppigel 305) and mixtures thereof may be included in the cosmetic compositions according to the invention.

Cosmetic compositions according to the present invention may additionally comprise an organic sunscreen. Suitable sunscreens may have UVA absorbing properties, UVB absorbing properties or a mixture thereof. The exact amount of the sunscreen active will vary depending upon the desired Sun Protection Factor, i.e., the "SPF" of the composition as well as the desired level of UVA protection. The compositions of the present invention preferably comprise an SPF of at least 10, preferably at least 15. SPF is a commonly used measure of photoprotection of a sunscreen against erythema. The SPF is defined as a ratio of the ultraviolet energy required to produce minimal erythema on protected skin to that required to products the same minimal erythema on unprotected skin in the same individual (see Federal Register, 43, No 166, pp. 38206-38269, Aug. 25, 1978).

Cosmetic compositions according to the present invention may comprise from about 2% to about 20%, preferably from about 4% to about 14%, by weight, of organic sunscreen. Suitable sunscreens include, but are not limited to, those found in the CTFA International Cosmetic Ingredient Dictionary and Handbook, 7$^{th}$ edition, volume 2 pp. 1672, edited by Wenninger and McEwen (The Cosmetic, Toiletry, and Fragrance Association, Inc., Washington, D.C., 1997).

A variety of additional optional ingredients may be incorporated into the compositions of the present invention. Non-limiting examples of these additional ingredients include additional skin care actives such as peptides (e.g., Matrixyl [pentapeptide derivative]), farnesol, bisabolol, phytantriol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; anti-acne medicaments (resorcinol, salicylic acid, and the like; antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol).

EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

A liquid foundation of the present invention is prepared as follows: in a suitable vessel, water, glycerine, disodium EDTA and benzyl alcohol are added and mixed using conventional technology until a clear water phase is achieved. When the water phase is clear, the methylparabens are added and mixed again until clear. The resultant phase is mixed with a Silverson SL2T or similar equipment on high speed (8,000 rpm, standard head). In a separate vessel, the KSG21, DC245, Pigment dispersion, other oils and the parabens are added and the mixture is milled using a Silverson SL2T on a high speed setting until a homogeneous mixture is created.

Following this step, the water phase and the silicone phase are combined and milled using the Silverson SL2T on a high speed setting until the water is fully incorporated and an emulsion is formed. The elastomer is then added and the mixture is mixed again using the Silverson on a high speed setting to generate the final product.

| Ingredient | Example # | | | | |
|---|---|---|---|---|---|
| | 1 | 2 | 3 | 4 | 5 |
| DC9040 cross linked elastomer gel[1] | 25.00 | 20.00 | | | 30.00 |
| KSG15 cross linked elastomer gel[2] | | | 20.00 | 50.00 | |
| Dimethicone copolyol cross-polymer (KSG21)[3] | | 5.00 | 10.00 | | 0.5 |
| Cyclomethicone (DC245) | 10.00 | 5.00 | 3.00 | 28.00 | 10.0 |
| PEG/PPG18/18 Dimethicone & Cyclomethicone (DC5185) | 1.8 | 2.0 | | | 2.2 |
| Octyl Methoxy cinnamate | 4.00 | | | | 2.00 |
| Octacrylene | | | | 4.00 | |
| Diethylhexyl carbonate (Tegosoft DEC) | 4.00 | | | | 2.00 |
| 4cst Dimethicone (DC5-2117) | | 4.00 | 1.9 | | |
| Fibril coated sunscreen grade Titanium dioxide 50% dispersion SAS/TTO-S-3/D5 | 6.0 | | | 6.00 | 6.00 |
| Fibril coated pigmentary grade Titanium dioxide 80% dispersion SA/NAI-TR-10/D5 | | 4.00 | | 8.00 | |
| Fibril coated pigment 50% dispersion SA/NAI-B-10/D5 | | | 0.2 | 0.1 | |
| Fibril coated sunscreen grade Titanium dioxide 40% dispersion M262 coated with 15% KP9909 | | | 8.00 | | |
| Titanium dioxide | 9.00 | 2.00 | 10.00 | | 10.00 |
| Iron oxides | 1.50 | 1.50 | 1.50 | 2.00 | 1.50 |
| Propylparabens | 0.1 | 0.1 | 0.1 | | 0.10 |
| Ethylparabens | 0.1 | 0.1 | 0.1 | | 0.20 |
| Methylparabens | 0.1 | 0.1 | 0.1 | | 0.10 |
| Disodium EDTA | 0.1 | 0.1 | 0.1 | | 0.01 |
| Benzyl alcohol | 0.5 | 0.5 | 0.5 | | 0.25 |
| Sodium chloride | 2.00 | 2.00 | 2.00 | | |
| Glycerin | 10.00 | 12.00 | | | 7.00 |
| Niacinamide | 2.00 | 5.00 | 5.00 | | 0.50 |
| Water | qs | qs | qs | Nil | qs |

[1]DC9040 comprises 11% solid organopolysiloxane elastomer in cyclopentasiloxane.
[2]KSG15 comprises 9% solid organopolysiloxane elastomer in cyclopentasiloxane.
[3]KSG21 comprises 27% solid organopolysiloxane elastomer in cyclopentasiloxane.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modification can be made without departing from the spirit and scope of the invention. It is therefore intended to cover in the appended claims all such changes and modifications that are within the scope of this invention.

What is claimed is:

1. A cosmetic composition comprising:
   (a) metal oxide particles having a coating of organo-functionalised silicone fibrils that are bonded to and extend away from the surface of the metal oxide particles; and
   (b) greater than about 1.7% by weight of the cosmetic composition of a cross-linked organopolysiloxane elastomer, wherein the fibrils are attached by treating the metal oxide particles with an organo-functionalised silicone polymer comprising a reactive moiety selected from the group consisting of amino, imino, halogen, hydroxyl, and alkoxyl, and wherein the fibril-coated metal oxide particles are coated with a hydrophobic coating.

2. The cosmetic composition of claim 1, wherein the organo-functionalised silicone polymer comprises from about 5 to about 100 silicone units.

3. The cosmetic composition of claim 1, wherein the organo-functionalised silicone polymer has a ratio (Mw/Mn) of weight-average molecular weight (Mw) to number-average molecular weight (Mn) from about 1.0 to about 1.3.

4. The cosmetic composition of claim 1, wherein the organo-functionalised silicone is a linear organo-functionalised silicone.

5. The cosmetic composition of claim 4, wherein the reactive moiety is located at one end of the molecular chain of the linear organo-functionalised silicone.

6. The cosmetic composition of claim 1, wherein the organo-functionalised silicone is a branched chain organo-functionalised silicone.

7. The cosmetic composition of claim 6, wherein the reactive moiety is located on a side chain.

8. The cosmetic composition of claim 7, wherein the side chain on which the reactive moiety is found is located within five silicone repeating units of one end of the silicone backbone.

9. The cosmetic composition of claim 1, wherein the metal oxide particles have a number weighted average secondary particle size from about 0.001 µm to about 100 µm.

10. The cosmetic composition of claim 9, wherein the metal oxide particles have a number weighted average secondary particle size from about 0.015 µm to about 10 µm.

11. The cosmetic composition of claim 10, wherein the metal oxide particles have a number weighted average secondary particle size from about 0.05 µm to about 1 µm.

12. The cosmetic composition of claim 1, wherein the metal oxide particles have a number weighted average primary particle size from about 10 µm to about 500 nm.

13. The cosmetic composition of claim 12, wherein the metal oxide particles have a number weighted average primary particle size from about 15 µm to about 100 nm.

14. The cosmetic composition of claim 13, wherein the metal oxide particles have a number weighted average primary particle size from about 20 µm to about 65 nm.

15. The cosmetic composition of claim 1, wherein the metal oxide particles are selected from the group consisting of titanium dioxide, zinc oxide, cerium oxide, zirconium oxide, iron oxide particles and mixtures thereof.

16. The cosmetic composition of claim 1, wherein the hydrophobic coating is manufactured by treating the surface of the metal oxide particles with a material selected from the group consisting of a reactive organo-polysiloxane, a polyolefin, a hydrogenated lecithin, a salt of hydrogenated lecithin, an N-acylamino acid, a salt of N-acylamino acid, a dextrin fatty acid ester, and mixtures thereof.

17. The cosmetic composition of claim 16, wherein the reactive organo-polysiloxane is selected from the group consisting of an organo hydrogen polysiloxane, a triorgano siloxy silicic acid, an organopolysiloxane modified at both terminal ends with trialkoxy groups, and mixtures thereof.

18. The cosmetic composition of claim 1, comprising from above about 1.7% to about 15% by weight of the cosmetic composition of cross-linked organopolysiloxane elastomer.

19. The cosmetic composition of claim 18, comprising from about 2% to about 10% by weight of the cosmetic composition of cross-linked organopolysiloxane elastomer.

20. The cosmetic composition of claim 19, comprising from about 2.2% to about 5% by weight of the cosmetic composition of cross-linked organopolysiloxane elastomer.

21. The cosmetic composition of claim 1, comprising from about 0.01% to about 15%, by weight of the cosmetic composition of emulsifying cross-linked organopolysiloxane elastomer.

22. The cosmetic composition of claim 21, comprising from about 0.01% to about 1% by weight of the cosmetic composition of emulsifying cross-linked organopolysiloxane elastomer.

23. The cosmetic composition of claim 1, comprising from about 0.01% to about 15% by weight of the cosmetic composition of non-emulsifying cross-linked organopolysiloxane elastomer.

24. The cosmetic composition of claim 23, comprising from about 2% to about 5% by weight of the cosmetic composition of non-emulsifying cross-linked organopolysiloxane elastomer.

25. The cosmetic composition of claim 1, additionally comprising from about 7% to about 80% by weight of the cosmetic composition of oil.

26. The cosmetic composition of claim 25, wherein the oil is selected from the group consisting of volatile oil, non-volatile oil and mixtures thereof.

27. The cosmetic composition of claim 26, wherein the volatile oil is selected from the group consisting of volatile cyclic silicone oil, volatile linear dimethicone having a viscosity from 2 to $50 \times 10^{-6}$ m$^2$/s (2-50 cst) and mixtures thereof.

28. The cosmetic composition of claim 27, wherein the ratio of volatile cyclic silicone oil to volatile linear dimethicone is from about 1:1 to about 25:1.

29. The cosmetic composition of claim 28, wherein the ratio of volatile cyclic silicone oil to volatile linear dimethicone is from about 5:1 to about 10:1.

30. The cosmetic composition of claim 1, additionally comprising an emulsifier.

31. The cosmetic composition of claim 30, wherein the emulsifier is selected from the group consisting of polyoxyalkylene copolymers, polyglyceryl copolymers and mixtures thereof.

32. The cosmetic composition of claim 30, wherein the emulsifier is free of a polyoxyalkylene emulsifier.

33. The cosmetic composition of claim 1 additionally comprising an organic sunscreen.

34. The cosmetic composition of claim 1, additionally comprising spherical polymeric particles having an average particle diameter from about 1 µm to about 50 µm.

35. The cosmetic foundation composition comprising a cosmetic composition according to claim 1.

36. A cosmetic composition comprising:
    (a) metal oxide particles having a coating of organo-functionalised silicone fibrils that are bonded to and extend away from the surface of the metal oxide particles and having a number weighted average primary particle size from about 15 nm to about 100 nm; and
    (b) greater than about 2% by weight of the cosmetic composition of cross-linked non-emulsifying organopolysiloxane elastomer, wherein the fibrils are attached by treating the metal oxide particles with an organo-functionalised silicone polymer comprising a reactive moiety selected from the group consisting of amino, imino, halogen, hydroxyl, and alkoxyl, and wherein the fibril-coated metal oxide particles are coated with a hydrophobic coating.

* * * * *